United States Patent [19]

Kress et al.

[11] Patent Number: 5,039,820

[45] Date of Patent: Aug. 13, 1991

[54] 4-AMINO-6-IODO-HEXAHYDROBENZ(C-D)INDOLES

[75] Inventors: Thomas J. Kress; James P. Wepsiec, both of Indianapolis, Ind.

[73] Assignee: Eli Lilly and Company, Indianapolis, Ind.

[21] Appl. No.: 485,193

[22] Filed: Feb. 26, 1990

[51] Int. Cl.$^5$ .......................................... C07D 209/90
[52] U.S. Cl. ................................................ 548/436
[58] Field of Search ....................................... 548/376

[56] References Cited

FOREIGN PATENT DOCUMENTS 3525564  2/1987  Fed. Rep. of Germany ...... 548/436

Primary Examiner—Mukund J. Shah
Assistant Examiner—Edward C. Ward
Attorney, Agent, or Firm—David E. Boone; Leroy Whitaker

[57] ABSTRACT

4-Amino-6-iodo-1,2,2a,3,4,5-hexahydrobenz[cd]indoles are useful intermediates to 4-amino-1,3,4,5-tetrahydrobenz [cd]indoles containing aminocarbonyl or alkoxycarbonyl substituents in the 6-position which are useful for the treatment of various disorders of the central nervous system.

8 Claims, No Drawings

4-AMINO-6-IODO-HEXAHYDROBENZ(CD)INDOLES

FIELD OF THE INVENTION

This invention relates to the fields of synthetic organic chemistry and pharmaceutical chemistry and provides valuable intermediates to compounds which are useful for the treatment of individuals suffering from or susceptible to various disorders of the central nervous system.

BACKGROUND OF THE INVENTION

Flaugh, U.S. Pat. No. 4,576,959, discloses a family of 6-substituted-4-dialkylamino-1,3,4,5-tetrahydrobenz[cd]indoles, described as central serotonin agonists and useful as anti-depressants. Flaugh discloses 6-bromo-1,2,2a,3,4,5-hexahydrobenz[cd]indoles as intermediates to certain of the disclosed compounds, in particular the 6-aminocarbonyl containing compounds. In the process disclosed by Flaugh, the bromo substituent is displaced with cyano by reaction with cuprous cyanide, and the cyano group is subsequently hydrolyzed to provide the aminocarbonyl substituent.

A method has been reported for preparing primary or secondary amides by reacting aryl, heterocyclic or vinylic halides with carbon monoxide and a primary or secondary amine in the presence of a palladium catalyst. (A. Schoenberg and R. F. Heck, *J. Org. Chem.*, 39, p. 3327, 1974) It has also been reported that esters can be formed using an alcohol in place of the amine in the catalyzed reaction. (A. Schoenberg, I. Bartoletti, and R. F. Heck, *J. Org. Chem.*, 39, p 3318, 1974) These references teach that aryl bromides and aryl iodides are both useful substrates for this palladium catalyzed carbonylation reaction.

We have discovered that while the 6-bromo-1,2,2a,3,4,5-hexahydrobenz[cd]indoles of Flaugh are unsuitable as substrates for this carbonylation reaction, the palladium-catalyzed reaction of 6-iodo-1,2,2a,3,4,5-hexahydrobenz[cd]indoles with carbon monoxide and ammonia is surprisingly facile, proceeding rapidly and in high yield to provide 6-aminocarbonyl-1,2,2a,3,4,5-hexahydrobenz[cd]indoles which can be converted to 6-aminocarbonyl-1,2,3,4-tetrahydrobenz[cd]indoles. It has also been found that alkyl and aryl substituted amides and esters in the 6-position can be prepared using amines or alcohols respectively with the 6-iodo-1,2,2a,3,4,5-hexahydrobenz[cd]indoles.

SUMMARY OF THE INVENTION

A compound of the formula:

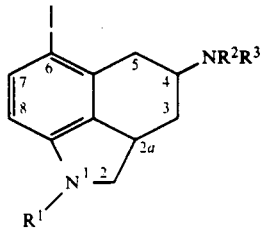

wherein
$R^1$ is hydrogen or an amino-protecting group;
$R^2$ is hydrogen, $C_1$-$C_4$ alkyl, allyl, or an amino-protecting group; and
$R^3$ is hydrogen, $C_1$-$C_4$ alkyl, or allyl.

DETAILED DESCRIPTION OF THE PREFERRED EMBODIMENTS

All temperatures used herein are expressed in degrees Celsius. The term "amino-protecting group" is used in this document as it is normally used in organic chemistry; therefore, the term refers to a group which can prevent an amino group from participating in a reaction carried out on some other functional group of the molecule, but which can be removed from the amine when it is desired to do so. Such groups are discussed by T. W. Greene in chapter 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, all of which are incorporated herein by reference. Examples of such groups include those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; benzyl and substituted benzyl such as 3,4-dimethoxybenzyl, o-nitrobenzyl, and triphenylmethyl; acyl and substituted acyl such as formyl, acetyl, chloroacetyl, dichloroacetyl, trichloroacetyl, trifluoroacetyl, phenoxyacetyl, benzoyl, and p-methoxybenzoyl; and other groups such as methanesulfonyl, p-toluenesulfonyl, p-bromobenzenesulfonyl, and p-toluenesulfonylaminocarbonyl.

The term "$C_1$-$C_4$ alkyl" includes methyl, ethyl, n-propyl, isopropyl, n-butyl, sec-butyl, and t-butyl.

The following compounds are set forth as examples of the compounds of this invention to assure the reader's understanding:

1-benzoyl-4-amino-6-iodo-1,2,2a,3,4,5-hexahydrobenz[cd]indole 1-acetyl-4-methylamino-6-iodo-1,2,2a,3,4,5-hexahydrobenz[cd]indole 1-trichloroacetyl-4-(di-n-propyl)amino-6-iodo-1,2,2a,3,4,5-hexahydrobenz[cd]indole 1-(t-butoxycarbonyl)-4-trifluoroacetylamino-6-iodo-1,2,2a,3,4,5-hexahydrobenz[cd]indole 1-phenoxyacetyl-4-(t-butyl)amino-6-iodo-1,2,-2a,3,4,5-hexahydrobenz[cd]indole 1-allyloxycarbonyl-4-allyloxycarbonylamino-6-iodo-1,2,2a,3,4,5-hexahydrobenz[cd]indole 1-benzoyl-4-(di-n-propyl)amino-6-iodo-1,2,2a,-3,4,5-hexahydrobenz[cd]indole 1-(2,2,2-trichloroethoxy)carbonyl-4-diethylamino-6-iodo-1,2,2a,3,4,5-hexahydrobenz[cd]indole 1-(p-toluenesulfonyl)-4-isopropylamino-6-iodo-1,2,2a,3,4,5-hexahydrobenz[cd]indole 1-benzoyl-4-(n-propyl)amino-6-iodo-1,2,2a,3,4,5-hexahydrobenz[cd]indole 1-(2,2,2-trichloroethoxy)carbonyl-4-(2,2,2-trichloroethoxy)carbonylamino-6-iodo-1,2,2a,3,4,5-hexahydrobenz[cd]indole 1-benzoyl-4-trifluoroacetylpropylamino-6-iodo-1,2,2a,3,4,5-hexohydrobenz[cd]indole Preferred embodiments of compounds of Formula I are those in which $R^1$ is an amino-protecting group, $R^2$ is hydrogen, n-propyl, or an amino-protecting group, and $R^3$ is hydrogen or n-propyl. It is frequently desirable that $R^1$ and $R^2$, when both are amino-protecting groups, be different in their reactivities toward the usual methods of removing such groups so that one of them may be removed while the other is left in place. Preferred amino-protecting groups for $R^1$ are acetyl, trichloroacetyl, trifluoroacetyl, p-toluenesulfonyl, and especially, benzoyl. When $R^2$ is an amino-protecting group, it is preferable that it be trifluoroacetyl.

Skilled artisans will recognize that the compounds of this invention have at least two chiral centers, one at the 2a-position and one at the 4-position. Therefore, there are at least four distinct stereoisomers of each compound of Formula I, more if there are chiral centers in the substituents. This invention provides all the various stereoisomers, whether in mixtures or in substantially pure form, but it is preferred that the compounds be substantially pure enantiomers.

A preferred starting material for the preparation of the compounds of this invention is the compound of the formula:

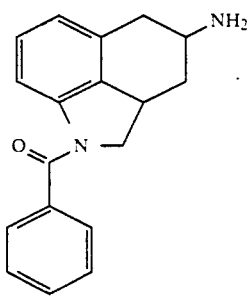

II which can be prepared by the method of Bach and Kornfeld, U.S. Pat. No. 4,110,339. The preferred starting material is a substantially pure enantiomer of the compound of Formula II, which can be prepared by the following method.

Either of the following pairs of enantiomers of 1-benzoyl-4,5-epoxy-1,2,2a,3,4,5-hexahydrobenz[cd]indole can be selectively prepared by the methods of Leanna, et al., Tet. Lett., 30, no. 30, pp. 3935–3938 (1989).

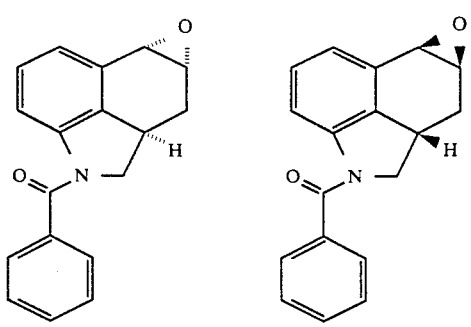

III$_a$        III$_b$ alpha-enantiomers

-continued

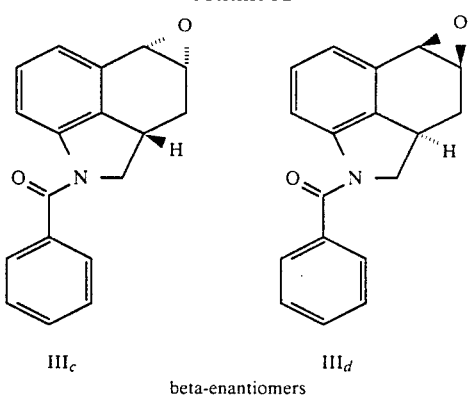

III$_c$        III$_d$ beta-enantiomers

The proper choice of the pair of enantiomers, III$_{a-b}$ or III$_{c-d}$, depends on the stereochemistry of the desired compound of Formula I which is to be prepared. For simplicity of discussion, the stereochemistry resulting from the alpha-enantiomers is illustrated below. Those skilled in the art will understand the manner in which the choice of the beta-enantiomers would affect the stereochemical configuration of subsequent intermediates and products.

The reaction of the racemic mixture of III$_a$ and III$_b$ with S-1-phenylethylamine produces a pair of diastereomers of the formulae:

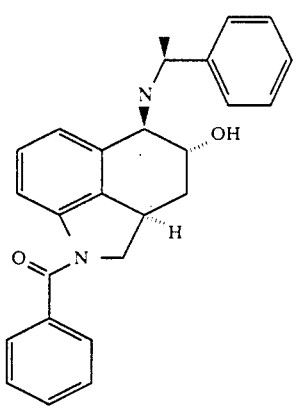

IV$_a$

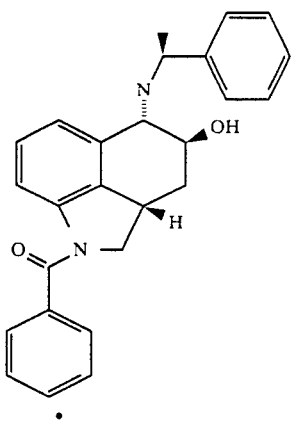

IV$_b$

The diastereomers can be separated by a number of methods frequently used in the art such as chromatography and selective crystallization.

A particularly advantageous method of preparing a substantially pure diastereomer of Formula IV$_a$ in a single step is as follows. The reaction is conducted in n-butanol at a concentration of about 1 gram of the alpha-enantiomers per 9 milliliters of solvent at about 90° for about 16 hours. Upon being cooled to about room temperature, the diastereomer of Formula IV$_b$ remains in solution, while the diastereomer of Formula IV$_a$ crystallizes and can be collected by filtration.

For simplicity of discussion, the subsequent intermediates and products shown below are those that result from the compound of Formula IV$_a$. Of course, the use of R-1-phenylethylamine instead of S-1-phenylethylamine results in the selective crystallization of the compound which is the mirror image of Formula IV$_a$, and the use thereof in this synthesis results in subsequent intermediates and products which are the enantiomers of those shown below.

The next step in the preparation of the preferred starting material for the compounds of the invention is to form an aziridine of Formula V. Several methods of forming aziridines from beta amino alcohols are known to the art. A preferred method is the reaction of the compound of Formula IV$_a$ with triethylamine and methanesulfonyl chloride in dichloromethane. The following aziridine compound of Formula V can be isolated from the reaction solution:

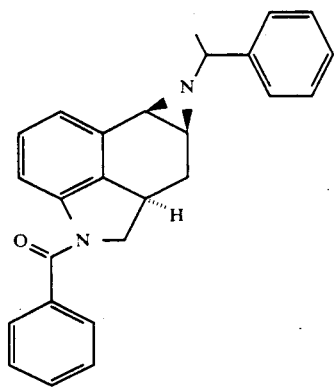

V

Of course the use of other enantiomers of Formula IV, or mixtures thereof, leads to different enantiomers of Formula V, or mixtures thereof.

The aziridine of Formula V is hydrogenolyzed over a noble metal catalyst such as palladium. A preferred solvent is a mixture of acetic acid and methanol, and the reaction is preferably conducted under approximately one atmosphere of hydrogen gas. The reaction mixture is stirred at about −5° until the aziridine is consumed, as determined by thin layer chromatography or liquid chromatography. The product of this hydrogenolysis is a secondary amine, 1-benzoyl-4- (S-1-phenylethyl)amino-1,2,2a,3,4,5-hexahydrobenz[cd]indole, which need not be isolated. The hydrogenolysis is continued at about 55° under about 1 atmosphere of hydrogen gas until the secondary amine is consumed, as determined by thin layer chromatography or liquid chromatography. Isolation, for example by crystallization, affords the substantially enantiomerically pure compound of Formula II which is:

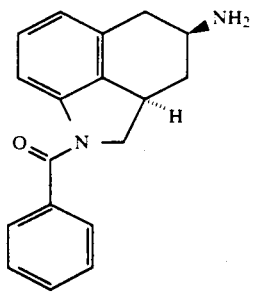

II$_a$

Of course, other enantiomers of the compounds of Formula II, or mixture thereof, are prepared from the corresponding enantiomers of the compound of Formula V.

Compounds of Formula I are prepared from the compound of Formula II, whether it exists as a mixture of stereoisomers or as a substantially pure enantiomer, using common reagents and methods well known in the art. A preferred method of introducing the iodo substituent at the 6-position is by reaction with iodine and orthoperiodic acid in the presence of an acid such as trifluoroacetic acid or sulfuric acid, in a solvent such as acetic acid. Another preferred method of iodination is by the use of N-iodosuccinimide in the presence of trifluoroacetic acid. Amino blocking groups can be added, if desired, to the 4-amino substituent using such methods as those disclosed by Greene, supra, and Barton, supra Alkyl groups can be added, if desired, to the 4-amino substituent using such common methods as ammonolysis of the appropriate halide as discussed by Morrison and Boyd, Chapter 22, *Organic Chemistry*, Third Edition, Allyn and Bacon, Boston, 1973. If desired, the benzoyl group can be removed from the 1-position using known methods and optionally replaced with other amino-protecting groups. The amino-protecting groups and alkyl groups can be added either before or after the iodination, as desired.

A preferred compound of Formula I, 1-benzoyl-4-(di-n-propyl)amino-6-iodo-1,2,2a,3,4,5-hexahydrobenz[cd]indole, can be prepared from the compound of Formula II$_a$ by iodination by iodine and orthoperiodic acid in the presence of an acid such as sulfuric acid or trifluoroacetic acid in a solvent such as aqueous acetic acid followed by alkylation with n-propyl iodide in the presence of a base such as potassium carbonate in a solvent such as acetonitrile. Alternatively, alkylation can precede iodination.

The compounds of Formula I are useful intermediates to the compounds of Flaugh, U.S. Pat. No. 4,576,959, in which the substituent at the 6-position is aminocarbonyl, or derivatives in which the substituent at the 6-position is alkyl or aryl substituted amides or alkyl- or aryl-carboxylic acid esters. The amino-carbonyl group can be introduced by reacting the compound of Formula I with ammonia and carbon monoxide in the presence of a palladium catalyst typical of those used in Heck reactions. The substituted amides can be introduced by using an amine instead of ammonia in the reaction. Carboxylic acid esters can be prepared by using alcohols in place of ammonia. The preferred palladium catalysts are bis(triphenylphosphine)palladium chloride and bis(triphenylphosphine)palladium bromide. Inert solvents such as acetonitrile or toluene are suitable. When ammonia is used, an approximately equimolar mixture of carbon monoxide and ammonia is supplied to the reaction at approximately one to approximately twenty atmospheres of pressure. When a reactant such as an amine or an alcohol is used in place of ammonia, the desired pressure of carbon monoxide is provided. The reaction vessel is then sealed and the reaction mixture is stirred at a temperature between about 25° C. and about 150° C. until the reactant is substantially consumed, as determined, for example, by thin layer chromatography or liquid chromatography. This Heck reaction can then be followed by reactions to remove any amino-protecting groups, add alkyl or allyl substituents to the amino group at the 4-position if so desired, and oxidize the bond between the 2- and 2a-positions to a double bond. Of course, modifications to this synthetic route may be desirable; however, it is frequently advantageous to perform the oxidation as the last chemical step.

The preparation of a preferred compound of Flaugh, 4-(di-n-propyl)amino-6-aminocarbonyl-1,3,4,5-tetrahydrobenz[cd]indole, from 1-benzoyl-4-(di-n-propyl)amino-6-iodo-1,2,2a,3,4,5-hexahydrobenz[cd]indole using carbon monoxide and ammonia is described hereinbelow.

The following examples are provided for the purpose of illustration and are not a limitation to the scope of the invention.

EXAMPLE 1

Preparation of (2a-R,4-S)-1-benzoyl-4-amino-1,2,2a,3,4,5-hexahydrobenz[cd]indole

Example 1A: Preparation of (2a-R,4-R,5-R)-1-benzoyl-4-(S-1-phenylethyl)amino-5-hydroxy-1,2,2a,3,4,5-hexahydrobenz[cd]indole A charge of (2a-RS,2a-$\alpha$,4-$\alpha$,5-$\alpha$)-1-benzoyl-4, 5-epoxy-1,2,2a,3,4,5-hexahydrobenz[cd]indole (482.5 grams (g), 1.74 moles) was dissolved in n-butanol (4400 milliliters (ml)) and split into two 5000-ml three-neck flasks, each one equipped with a mechanical stirrer, a thermocouple and a condenser topped with a nitrogen inlet. The (S)-1-phenylethylamine (900 ml total; 450 ml, 6.98 moles to each flask) was added and the solution was stirred at 90° overnight. A small aliquot was taken and the n-butanol was removed in vacuo for thin layer chromatography (SiO$_2$, 1:1 hexanes:ethyl acetate) which showed no starting material after 24 hours. The reaction mixture was allowed to cool to room temperature, whereupon the desired amino alcohol crystallized directly from the reaction mixture. The crystalline material was filtered, washed with diethyl ether (2000 ml for each section), and dried. The first crop, both sections combined, was 168.26 g of the desired product and was used directly in the subsequent reaction. A second crop was obtained by evaporation of the above filtrates to dryness, dissolution in toluene (200 ml), and the addition of hexanes (100 ml) and diethyl ether (100 ml). The resulting solution was allowed to stand in the refrigerator overnight to provide an additional 39.2 g of the desired product after filtration. The recovered product was analyzed by infrared spectroscopy (IR) and nuclear magnetic resonance spectroscopy (NMR), mass spectrometry (MS), ultraviolet spectroscopy (UV), thin layer chromatography (TLC). An elemental analysis was also performed. The following results were obtained identifying the product (2a-R,4-R,5-R)-1-benzoyl-4-(S-1-phenylethyl)amino-5- hydroxy-1,2, 2a,3,4,5-hexahydrobenz[cd]indole.

PHYSICAL DATA m.p.: 158°–160°

IR: 3480 (br), 1638 (s), 1610 (w), 1470 (s), 1457 (s), 1394 (s) cm$^{-1}$:

NMR: ($^1$H, ppm, CDCl$_3$): 7.02–7.56 (m, 13H), 4.21 (q, 1H, J=6.6 Hz), 4.25 (br s, 1H), 3.63 (m, 2H), 3.42 (m, 2H), 2.72 (br s, 1H, exchanges with D$_2$O), 1.99 (m, 1H), 1.80 (m, 1H), 1.47 (d, 3H, J=6.6 Hz).

M.S.: m/e=398, 355, 249, 145, 105.

U.V.: $\lambda_{max}$=292 ($\epsilon$=8930), 265 ($\epsilon$=11400) in ethanol.

TLC: R$_f$=0.68 (SiO$_2$, 42:42:16 ethyl acetate:hexane:triethylamine)=desired diastereomer R$_f$=0.62 (SiO$_2$, 42:42:16 ethyl acetate:hexane:triethylamine)=undesired diastereomer R$_f$=0.36 (SiO$_2$, hexane:ethyl acetate 1:1)=amino alcohols (mixture).

| Analysis: | C | H | N |
| --- | --- | --- | --- |
| theory | 78.37 | 6.58 | 7.03 |
| found | 78.14 | 6.67 | 6.77 |

$[\alpha]_D$= −37.58° (589 nm).

Example 1B: Preparation of (2a-R,4-S,5-R)-1-benzoyl-4,5-(S-1-phenylethyl)azirino-1,2,2a,3,4,5-hexahydrobenz[cd]indole A solution of the compound prepared by the method of Example 1A (749.5 g) in methylene chloride (6000 ml) was cooled to −10° under an atmosphere of nitrogen. Triethylamine (590 g, 3.1 equiv) was then added to the mixture, followed by the dropwise addition of methanesulfonyl chloride (330 g, 1.5 equiv) at a rate to maintain the temperature below 0°. When the addition of methanesulfonyl chloride was complete, the reaction mixture was stirred at 0° for an additional 0.5 hour, followed by warming to room temperature. The reaction mixture was then washed successively with water (6000 ml), 5% aqueous sodium bicarbonate (6000 ml), and brine (6000 ml). The organic phase was then dried over sodium sulfate (250 g) and filtered. Acetonitrile (3000 ml) was added to the filtrate. The volume was reduced by evaporation in vacuo to approximately 3000 ml, whereupon a precipitate formed. Additional acetonitrile (3000 ml) was added, and the volume was reduced to 2000 ml by evaporation in vacuo. The resulting suspension was cooled with an ice bath and stirred for 1.5 hours. The precipitate was filtered, washed with cold acetonitrile, and dried in vacuo at 50° to afford 607.5 g of a product having the following analysis corresponding to (2a-R,4-S,5-R)-1-benzoyl-4, 5-(S-1-phenylethyl)azirino-1,2,2a,3,4,5-hexahydrobenz[cd]indole.

PHYSICAL DATA m.p.: 172°–176°

NMR: Structure verifed.

($^{13}$C, ppm, CDCl$_3$): 168.6, 144.4, 141.6, 136.5, 132.8, 130.5, 128.6, 128.3, 127.3, 127.0, 126.7, 124.1, 69.9, 59.0, 38.6, 37.7, 34.5, 31.6, 23.6.

M.S.: m/e=380, 275, 261, 105, 77.

U.V.: $\lambda_{max}$=302 ($\epsilon$=8730), 272 ($\epsilon$=14000) in ethanol.

TLC: R$_f$=0.72 (SiO$_2$, hexane:ethyl acetate 1:1)=desired diastereomer R$_f$=0.60 (SiO$_2$, hexane:ethyl acetate 1:1)=undesired diastereomer R$_f$=0.28 (SiO$_2$, hexane:ethyl acetate 1:1)=amino alcohol $R_f=0.16$ (SiO$_2$, hexane:ethyl acetate 1:1)=triphenylphosphine oxide $R_f=0.47$ (SiO$_2$, hexane:ethyl acetate 1:1)=reduced DEAD Visualization by UV and by iodine stain.

| Analysis: | C | H | N |
|---|---|---|---|
| theory | 82.07 | 6.37 | 7.36 |
| found | 81.79 | 6.34 | 7.28 |

$[\alpha]_D = +32.75°$ (589 nm).
$[\alpha]_D = +146.90°$ (365 nm).

Example 1C: Preparation of (2a-R,4-S)-1-benzoyl-4-amino1,2,2a,3,4,5-hexahydrobenz[cd]indole A 500-ml, 3-neck round bottom flask equipped with a mechanical stirrer, a thermocouple and a condenser topped with a three-way gas/vacuum adapter was charged with the compound prepared by the method of Example 1B (19.0 g, 0.050 mole) followed by the addition of a precooled (−5°) solution of glacial acetic acid:methanol (170 ml:70 ml). The resulting solution was stirred at −5° and the atmosphere was replaced with nitrogen. A suspension of 10% Pd/C (8.50 g) in glacial acetic acid (40 ml) was added, the atmosphere was replaced with hydrogen at about atmospheric pressure, and the reaction mixture was stirred at −5° for 2 hours. The reaction mixture was then stirred at 55° for an additional 6 hours to complete the second reduction, namely cleavage of the chiral phenylethyl auxiliary. The reaction mixture was cooled to room temperature, filtered through filter aid, and washed with acetic acid (5×50 ml), and the filtrate was concentrated in vacuo at 30° C. To the gummy residue was added methylene chloride (200 ml) and 1N hydrochloric acid (200 ml). The layers were separated, and the organic phase was extracted with another portion of 1N hydrochloric acid (2×100 ml). The combined aqueous phase was made basic with 5N sodium hydroxide and exhaustively extracted with methylene chloride (200 ml+2×100 ml). The combined organic phase was dried over brine, then sodium sulfate. Removal of the solvent in vacuo afforded 12.46 g of (2a-R,4-S)-1-benzoyl-4-amino-1,2,2a,3,4,5-hexahydrobenz[cd]indole which crystallized upon standing. Recrystallization from either isopropanol or 50% aqueous ethanol afforded short needle-like crystals having the following analytical results.

PHYSICAL DATA m.p.: 147°–150°.
IR: 1225 (w), 1396 (s), 1457 (s), 1488 (m), 1597 (m), 1612 (s), 1637 (s), 3009 (m) cm$^{-1}$.
NMR: ($^1$H, ppm, CDCl$_3$): 7.38–7.57 (m, 5H), 6.99 (m, 1H), 6.78 (m, 2H), 4.25 (br m, 1H), 3.62 (t, 1H, J=11.5 Hz), 3.29 (m, 2H), 3.12 (dd, 1H, J=6.1, 16.7 Hz), 2.39 (dd, 1H, J=10.3, 16.7 Hz), 2.17 (m, 1H), 1.49 (br s, 2H), 1.31 (q, 1H, J=11.5 Hz). ($^{13}$C, ppm, CDCl$_3$): 168.5, 141.4, 136.6, 133.3, 132.6, 130.7, 130.1, 128.8, 128.1, 127.7, 127.6, 127.1, 123.1, 122.6, 58.2, 48.6, 37.3, 37.2, 36.9.
M.S.: m/e=278, 261, 235, 130, 105, 77.
U.V.: $\lambda_{max}=291$ ($\epsilon=8150$), 266 ($\epsilon=10600$) in ethanol.
TLC: $R_f=0.19$ (SiO$_2$, CH$_2$Cl$_2$:methanol 4:1)=desired product. $R_f=0.41$ (SiO$_2$, ethyl acetate:hexanes 1:1)=aziridine. $R_f=0.86$ (SiO$_2$, CH$_2$Cl$_2$:methanol 4:1)=secondary amine. $R_f=0.13$ (SiO$_2$, ethyl acetate:hexanes 1:1)=secondary amine. Visualization by UV and by iodine stain.

| Analysis: | C | H | N |
|---|---|---|---|
| theory | 77.67 | 6.52 | 10.06 |
| found | 77.76 | 6.55 | 9.61 |

$[\alpha]_D = +57.43$ (589 nm).
$[\alpha]_D = +341.58$ (365 nm).

EXAMPLE 2

Preparation of (2a-R,4-S)-1-benzoyl-4-amino-6-iodo-1,2,2a,3,4,5-hexahydrobenz[cd]indole Into a 50-ml flask, equipped with a magnetic stir bar, were placed acetic acid (10 ml), water (2 ml), the (2a-R,4-S)-1-benzoyl-4-amino-1,2,2a,3,4,5-hexahydrobenz[cd]indole prepared by the method of Example 1 (500 milligrams (mg), 1.8 millimoles (m moles), trifluoroacetic acid (277 microliters, 3.6 m moles), orthoperiodic acid (103 mg, 0.45 milligram moles), and iodine (233 mg, 0.9 m moles); all were combined in the flask at approximately room temperature. The reaction mixture was heated to 70° C., with the flask being continually purged with nitrogen. The temperature was maintained at 70° C. for one hour and forty-five minutes, after which the reaction mixture was cooled to 0° C. An aqueous solution of sodium bisulfite, 10% by weight, (approximately 5 ml) was added to destroy any excess iodine or orthoperiodic acid. Methylene chloride (10 ml) was added to the flask. Ammonium hydroxide, concentrated aqueous solution, (20 ml) was added dropwise; after the addition of the ammonium hydroxide, the pH of the aqueous phase was approximately 10. The reaction mixture was transferred to a separatory funnel. The reaction flask was rinsed with methylene chloride (twice, 10 ml each time), which was also added to the separatory funnel. The phases were separated, and the aqueous phase was extracted with methylene chloride (2×20 milliliters). The combined organic phases were extracted with saturated aqueous sodium chloride (20 ml), and then dried over anhydrous magnesium sulfate. Evaporation in vacuo of the solvent afforded a very light yellow, foamy solid (640 mg). The solid provided the following physical data corresponding to (2a-R,4-S)-1-benzoyl-4-amino-6-iodo-1,2,2a,3,4, 5-hexahydrobenz[cd]indole.

IR: (KBr): 3450 (br), 2915 (w), 2870 (w), 1641 (s), 1600 (w), 1577 (w), 1465 (w), 1451 (s), 1379 (s) cm$^{-1}$.
NMR: ($^1$H, ppm, CDCl$_3$): 7.3–7.7 (m, 7H), 4.25 (br m, 1H), 3.65 (t, 1H), 3.30 (m, 2H), 3.05 (dd, 1H), 2.3–2.05 (m, 2H), 1.50 (br s, 2H) 1.30 (q, 1H)
M.S.: m/e=404.

EXAMPLE 3

Preparation of (2a-R,4-S)-1-benzoyl-4-(di-n-propyl)amino-6-iodo-1,2,2a,3,4,5-hexahydrobenz[cd]indole Example 3A Into a 100-ml flask, equipped with a magnetic stir bar, was placed the (2a-R,4-S)-1-benzoyl-4-amino-6-iodo-1,2,2a,3,4,5-hexahydrobenz[cd]indole prepared by the method of Example 2 (630 mg, 1.56 m moles) and acetonitrile (20 mg). Potassium carbonate (1.08 g, 7.8 m moles) was ground with a hot mortar and pestle, then added to the flask. 1-Iodopropane (769 microliters, 7.8 m moles) was added. The reaction mixture was stirred at 70° C. under a nitrogen purge for 28 hours. The salt which was a byproduct of the reaction was filtered from the reaction mixture and washed with acetonitrile (2×25 ml), which was added to the filtrate. The solvent was removed in vacuo from the filtrate. The residual orange paste was taken up in a mixture of ethyl acetate (50 ml) and water (25 ml). The organic phase was separated from the aqueous phase, washed with water (2×25 ml), and dried over anhydrous sodium sulfate. The solvent was removed in vacuo to afford a light brown solid (650 mg). The solid product had the same nmr spectrum as the product from Example 3B.

Example 3B: Alternative procedure

Fifty milliliters of a solution of 1-benzoyl-4-(di-n-propyl)amino-1,2,2a,3,4,5-hexahydrobenz[cd]indole (approximately 500 milligrams, approximately 1.4 m moles) in acetonitrile was placed into a 100 milliliter flask. The solvent was removed in vacuo to afford a viscous oil. To the oil was added a mixture of acetic acid, water and sulfuric acid (25 ml, 100:20:3 by volume). To the resulting solution was added orthoperiodic acid (96 mg, 0.42 m moles) and iodine (218 mg, 0.89 m moles). The reaction mixture was heated to 70° C. and maintained at that temperature, under nitrogen purge, for 25 minutes. The solvent and excess iodine were removed in vacuo. The residue was taken up in water (50 ml). An addition of aqueous sodium hydroxide (5 Normla (N), 15 ml) raised the pH to approximately 12 and caused the precipitation of a solid. The mixture was cooled to approximately 0° C. The solid was filtered, washed with water (3 times, 30 ml each), and dried in vacuo to afford a tan solid (619 mg). This material, provided the following data corresponding to (2a-R,4-S)-1-benzoyl-4-(di-n-propyl)amino-6-iodo-1,2,2a,3,4,5-hexahydrobenz[cd]indole.

IR: (CHCl$_3$): 3010 (w), 2961 (m), 2934 (m), 2870 (w), 1638 (s), 1467 (s), 1453 (s), 1382 (s), 1222 (w) cm$^{-1}$

NMR: ($^1$H, ppm, CDCl$_3$): 7.3–7.7 (m, 7H), 4.25 (br m, 1H), 3.65 (t, 1H), 3.30 (m, 1H), 3.20 (m, 1H), 2.80 (dd, 1H), 2.45 (m, 5H), 2.15 (m, 1H), 1.25–1.60 (m, 5H), 0.90 (t, 6H)

M.S.: m/e=448.

| Analysis: | C | H | N |
|---|---|---|---|
| Theory | 59.02 | 5.98 | 5.73 |
| found | 58.78 | 6.04 | 5.68 |

EXAMPLE 4

Preparation of (2a-R,4-S)-1-benzoyl-4-(tri-fluoroacetyl)amino-6-iodo-1,2,2a,3,4,5-hexahydrobenz[cd]indole Into a 200-ml flask was placed (2a-R,4-S)-1-benzoyl-4-amino-1,2,2a,3,4,5-hexahydrobenz[cd]indole prepared by the method of Example 1 (1.00 gram, 3.6 m mole), methylene chloride (20 ml), and trifluoroacetic anhydride (2 portions, 564 microliters each, 4.0 m moles each). The reaction mixture was stirred at room temperature for one hour. A third portion of trifluoroacetic anhydride (564 microliters, 4.0 m moles) was added, and the reaction mixture was stirred at room temperature for one hour. The solvent was removed in vacuo to afford a tan paste, to which was added orthoperiodic acid (210 mg, 0.9 m moles), a mixture of acetic acid, water, and sulfuric acid (50 ml, 100:20:3 by volume), and iodine (460 mg, 1.8 m moles). The reaction mixture was heated to 70° C. under nitrogen purge for 1 hour. Aqueous sodium bisulfite (15 ml, 10% by weight) was added while the temperature of the reaction mixture was maintained at 70° C. Water (100 ml) was added to the warm reaction mixture, which was then cooled to −20° C. The precipitated product was filtered, washed with water (200 ml), and dried in vacuo at 70° C. to afford a fluffy, yellow solid (1.6 g). Analysis of the solid provided the following data.

IR: (KBr): 3270 (br), 3100 (w), 2940 (w), 2860 (w), 1701 (s), 1662 (s), 1565 (s), 1466 (s), 1453 (s), 1370 (s), 1354 (s) cm$^{-1}$.

NMR: ($^1$H, ppm, DMSO-d6): 9.60 (d, 1H), 7.4–7.7 (m, 7H), 4.25 (m, 1H), 4.15 (m, 1H), 3.80 (m, 1H), 3.45 (m, 1H), 2.87 (dd, 1H), 2.45 (dd, 1H), 2.10 (m, 1H), 1.45 (q, 1H).

M.S.: m/e=500.

| Analysis: | C | H | N |
|---|---|---|---|
| Theory | 48.02 | 3.22 | 5.60 |
| Found | 48.20 | 3.22 | 5.76 |

EXAMPLE 5

Preparation of 1-Benzoyl-4-Benzyloxycarbonyl-6-iodo-1,2,2a,3,4,5-hexahydrobenz[cd]indole Into a 5-ml flask was placed (2a-R, 4-S)-1-benzoyl-4-amino-1,2,2a,3,4,5-hexahydrobenz[cd]indole prepared by the method of Example 1 (100 mg, 0.36 m mole), methylene chloride (5 ml), triethyl amine (56 microliters, 0.40 m mole), and benzyl chloroformate (57 microliters, 0.40 m mole). The mixture was stirred at room temperature for about 15 minutes. The solvent was removed in vacuo to afford a white solid. To the white solid was added a mixture of acetic acid, water and sulfuric acid (10 ml, 100:20:3 by volume), orthoperiodic acid (21 mg, 0.09 m mole), and iodine (46 mg, 0.18 m mole). The mixture was heated to 55° C., stirred at that temperature for approximately 1 hour, then cooled to 30° C. Aqueous sodium bisulfite (10% by weight, 2 ml) was added to reduce the excess iodine. Water (25 ml) was added dropwise with stirring. The light yellow solid which precipitated upon the addition of the water was collected by vacuum filtration, washed with water, and dried on the filter. The solid (199 mg) was purified by liquid chromatography (6 g of silica packing, 9:1 by volume methylene chloride:diethyl ether eluent). The eluted fractions were analyzed by thin layer chromatography (silica, 9:1 by volume methylene chloride:diethyl ether). Fractions containing the product were combined and evaporated in vacuo to afford (2a-R,4-S)-1-benzoyl-4-amino-1,2,2a,3,4,5hexahydrobenz[cd]indole (120 mg) which provided the following analytical results.

IR: (CHCl$_3$): 1719 (br), 1635 (br), 1510 (br), 1468 (s), 1454 (s), 1380 (br) cm$^{-1}$.

NMR: ($^1$H, ppm, DMSO-d6): 7.2–7.7 (m, 12H), 5.0 (s, 2H), 4.05 (br m, 1H), 3.85 (m, 1H), 3.75 (m, 1H), 3.40 (m, 1H), 2.85 (dd, 1H), 2.25 (dd, 1H), 2.05 (m, 1H), 1.15 (q, 1H).

M.S.: m/e=538.

| Analysis: | C | H | N | I |
|---|---|---|---|---|
| Theory | 58.00 | 4.31 | 5.20 | 23.57 |

| Analysis: | C | H | N | I |
|---|---|---|---|---|
| Found | 58.24 | 4.26 | 5.07 | 22.38 |

EXAMPLE 6

Preparation of
(2a-R,4-S)-4-(di-n-propyl)amino-6-aminocarbonyl-
1,3,4,5-tetrahydrobenz[cd]indole Example 6A. Preparation of
1-benzoyl-4(di-n-propyl)amino-6-aminocarbonyl-
1,2,2a,3,4,5-hexahydrobenz[cd]indole Into an autoclave were placed (2a-R,4-S)-1-benzoyl-4-(di-n-propyl)amino-6-iodo-1,2,-2a,3,4,5-hexahydrobenz[cd]indole prepared by the method of Example 3 (1.33 g, 2.7 m moles) dissolved in toluene (100 ml) and bis(triphenylphosphine)palladium bromide (111 mg, 0.14 m mole). The autoclave was assembled and purged with carbon monoxide. The autoclave and its contents were cooled to 0° C., and the pressure was raised to 50 pounds per square inch gauge (psig) (3.515 kilograms per square centimeter) with anhydrous ammonia. The pressure in the autoclave was then raised to 100 psig (7.03 Kg per square cm) with carbon monoxide and the autoclave was sealed. The reaction mixture was heated to 100° C. and stirred for 6 hours. The reaction mixture was stored in the closed autoclave at room temperature overnight. The reaction mixture was filtered, and the autoclave was rinsed with toluene (25 ml), which was then filtered and added to the first filtrate. The filtrate was extracted first with aqueous sodium hydroxide (1.0 N, 20 ml) and twice with saturated aqueous sodium chloride (25 ml each time). The toluene phase was dried over anhydrous sodium sulfate, filtered, and evaporated in vacuo to afford a dark yellow solid. The solid was taken up in ethyl acetate (5 ml). Hexane (15 ml) was added, and the resulting mixture was heated on a steam bath. Ethyl acetate (approximately 1 ml) was added to completely dissolve the solid, and the solution was allowed to cool to room temperature overnight. The mixture was cooled to −30° C. The mixture was filtered and the solid was washed with hexane. The solid was taken up in methylene chloride (20 ml), and the solvent was evaporated in vacuo. Again the solid was taken up in methylene chloride (20 ml), and the solvent was evaporated in vacuo to afford a tan solid. This solid product provided the same nmr spectrum as the product of Example 6B.

Example 6B: Preparation of
4-(di-n-propyl)amino-6-aminocarbonyl-1,2,2a,3,4,5-hexahydrobenz[cd]indole Into an autoclave were placed (2a-R,4-S)-1-benzoyl-4-(di-n-propyl)amino-6-iodo-1,2,2a,3,4, 5-hexahydrobenz[cd]indole, prepared by the method of Example 3 (16.5 g, 33.8 m moles) and dissolved in toluene (150 ml), and bis(triphenylphosphine)palladium chloride (from Alfa Products 1.19 g, 1.69 m moles). The autoclave was assembled and purged with carbon monoxide four times. The autoclave and its contents were cooled in an ice bath to a temperature of about 0° C. Anhydrous ammonia was introduced with stirring to a final pressure of about 50 psig (3.515 kg per square cm). Carbon monoxide gas was introduced with stirring to a final pressure of 100 psig (7.03 kg per square cm) at 0° C. The autoclave was sealed and heated to 100° C. with stirring. The initial pressure in the vessel was about 270 psig (18.98 kg per square cm) at 100° C. The reaction mixture was heated at 100° C. for 4.5 hours. The reaction mixture was left at room temperature in the autoclave overnight under carbon monoxide atmosphere. The autoclave was vented and opened and yellow crystalline solid was observed on the paddles and vessel walls. The liquid phase was filtered and the yellow solid was dissolved in methylene chloride (100 ml). The autoclave vessel and paddles were rinsed with methylene chloride (50 ml) and the methylene chloride solution was filtered and combined with the toluene solution. The combined organic phase was extracted with one normal sodium hydroxide (50 ml) with an emulsion being formed. A saturated sodium chloride solution was added (200 ml) and the mixture shaken to break the emulsion. The lower aqueous phase was removed and the upper organic phase was extracted two times with saturated sodium chloride solution (200 ml each time). The organic phase was dried with anhydrous sodium sulfate and one spatala of carbon black was added to the mixture. The resulting mixture was filtered, the solid was washed with methylene chloride and the resulting solvent volume reduced to about 100 ml by vacuum. This liquid was refiltered to remove any remaining carbon. The liquid was allowed to cool to room temperature and after a substantial amount of solid material crystallized the mixture was cooled to about −30° C. overnight. The cold mixture was filtered and the resulting solid rinsed with hexane (two times with 50 milliliter aliquots). The solid was suctioned dried to provide 10.6 g of off-white crystalline solid. The solid was dried in a vacuum oven for about five hours to provide 9.1 g of an off-white crystalline solid. The solid was analyzed to produce the following results corresponding to the above-named hexahydrobenz[cd]indole.

IR: (KBr): 3347 (br), 3177 (br), 2958 (s), 2932 (s), 2871 (s), 1676 (br), 1639 (br), 1579 (s), 1465 (s), 1450 (s), 1368 (br) cm$^{-1}$.

NMR: ($^1$H, ppm, CDCl$_3$): 7.3–7.7 (m, 7H), 5.80 (br s, 2H), 4.30 (br m, 1H), 3.65 (t, 1H), 3.1–3.4 (m, 3H), 2.90 (dd, 1H), 2.45 (m, 4H), 2.20 (m, 1H), 1.40 (m, 5H), 0.90 (t, 6H).

M.S.: m/e=405.

Example 6C. Preparation of
4-(di-n-propyl)-amino-6-aminocarbonyl-1,2,2a,3,4,5-hexahydrobenz[cd]indole Into a 500-ml Morton flask were added 1-benzoyl-4-(di-n-propyl)amino-6-aminocarbonyl-1,2,2a,3,4, 5-hexahydrobenz[cd]indole (6.65 g, 16.4 m moles) prepared by the method of Example 6B and tetrahydrofuran (140 ml) which had been dried over molecular sieve. The flask was sealed and purged with nitrogen. The reaction mixture was cooled to about −78° C. in a dry acetone bath with stirring. A hexane solution of N-butyl lithium (41 ml of 1.6 molar butyl lithium solution, 65.6 milligram moles butyl lithium) was added dropwise with stirring to the cold reaction mixture. The reaction mixture was stirred at −78° C. under a nitrogen atmosphere for about one hour. The reaction was quenched by adding acetic acid (4.7 ml, 82 m moles) dropwise to the mixture maintained at −78° C. The cold bath was removed and stirring was continued while the orange color slowly dissipated to provide a thick tan slush. After the orange color dissipated but before the reaction mixture had warmed to room temperature, an aqueous solution of hydrochloric acid was added (140 ml, 1.0 N) dropwise with stirring. The two-phase mixture was poured into a separatory funnel and 140 ml of methylene chloride were added. After shaking, the lower organic phase was drained off. The acidic aqueous phase was extracted with methylene chloride (three times with 40 ml aliquots). An aqueous sodium hydroxide solution (70 ml, 5.0 N) was added dropwise with stirring to the aqueous phase to provide a pH of about 12. A white solid precipitated. The suspension was extracted with methylene chloride (four times with 50 ml aliquots). The methylene chloride phases were combined and dried with anhydrous sodium sulfate. The dried methylene chloride was filtered into a tared flask and the remaining solids rinsed with three aliquots of methylene chloride. The methylene chloride solution was evaporated to dryness under vacuum to provide 4.63 g of solid.

IR: (KBr): 3392 (br), 3180 (br), 2957 (m), 2934 (m), 2870 (w), 2810 (w), 1654 (s), 1584 (s), 1457 (s), 1380 (s), 1350 (s) cm$^{-1}$.

NMR: ($^1$H, ppm, CDCl$_3$): 7.30 (d, 1H), 6.40 (d, 1H), 5.7 (br s, 2H), 3.9 (m, 1H), 3.70 (m, 1H), 3.05–3.30 (m, 4H), 2.85 (dd, 1H), 2.45 (m, 4H), 2.15 (m, 1H), 1.45 (m, 4H), 0.90 (t, 6H).

M.S.: m/e=301.

Example 6D. Preparation of 4-(di-n-propyl)amino-6-aminocarbonyl-1,3,4,5-tetrahydrobenz[cd]indole Manganese dioxide (43.3 g, 498 m moles) was suspended in 1,2-dichloroethane (400 ml) in a 2-liter flask. The manganese dioxide suspension was cooled to −5° C., and acetic acid was added to the flask (300 ml). The manganese dioxide suspension was again cooled to −5° C. 4-(di-n-propyl)amino-6-aminocarbonyl-1,2,2a,3,4,5-hexahydrobenz[cd]indole (100 g, 332 m moles) was dissolved in acetic acid (300 ml). The solution was added to the manganese dioxide suspension while the temperature was maintained between −6° and 0° C. The reaction mixture was stirred for 2.5 hours. Filter aid (45 g) was added to the reaction mixture, which was then filtered. The filter cake was washed with acetic acid (600 ml) and dichloroethane (800 ml). The filtrate was evaporated in vacuo. The residue was taken up in toluene (500 ml), and the solution was evaporated in vacuo. The residue was again taken up in toluene (500 ml), and the solution was evaporated in vacuo. To the residue (186 g) was added aqueous sodium hydroxide (2.0 N, 700 ml). The mixture was stirred for 30 minutes, and filter aid (45 g) was added to the mixture. The mixture was filtered, and the filter cake was washed with 1,2-dichloroethane (500 ml). The organic phase of the filtrate was washed with water (700 ml), washed with saturated sodium chloride (700 ml), and then dried over sodium sulfate. The solvent was evaporated in vacuo to afford 96.8 g of the desired compound which was identified by comparison of nmr spectrum with the known compound.

EXAMPLE 7

Preparation of 1-benzoyl-4-(trifluoroacetyl)amino-6-ethoxycarbonyl-1,2,2a,3,4,5-hexahydrobenz[cd]indole Into an autoclave were placed 1-benzoyl-4-(trifluoroacetyl)amino-6-iodo-1,2,2a,3,4,5-hexahydrobenz[cd]indole (500 mg, 1 mmole), bis(triphenylphosphine)palladium chloride (50 mg), triethylamine (0.5 ml) and ethanol (200 ml). The autoclave was flushed three times with carbon monoxide and then pressured to 100 psig (7.03 Kg per square cm) at room temperature. The reaction mixture was heated to 130° C. and maintained a temperature of about 125° C. for 2 hours. The pressure in the vessel increased to 150 psig (10.5 Kg per square cm guage) during the heating. The heater was removed and the mixture was allowed to cool to 25° C. The contents of the reactor were poured into a round bottom flask. The liquid was removed by vacuum providing 690 mg of white residue The residue was dissolved in a mixture of methylene chloride and water. The methylene chloride phase was separated and washed one time with water. The organic layer was dried over magnesium sulfate and evaporated to afford 450 mg of a white solid. The solid was dissolved in 10 ml of boiling toluene which was then cooled and the solid crystallized. The crystals were filtered and dried to provide 330 mg of fine needle crystals which provided the following analytical results.

m.p.: 240°–241° C.

U.V.: (ethanol) $\lambda_{max}$=305 ($\epsilon$=18900), 290 ($\epsilon$=18000)

M.S. m/e=446 (18%), 400 (4%), 333 (3%), 105 (100%), 77 (49%).

I.R.: (CHCl$_3$) 3019, 1723, 1706, 1453, 1380, 1366, 1269, 1226, 1218, 1206, 1178.

NNR: (CDCl$_3$) showed presence of one ethyl group.

| Analysis: | C | H | N |
|---|---|---|---|
| Theory | 61.88 | 4. | 6.28 |
| Found | 61.62 | 4.73 | 6.12 |

EXAMPLE 8

Preparation of 1-benzoyl-4-(trifluoroacetyl)amino-6-ethoxycarbonyl-1,2,2a,3,4,5-hexahydrobenz[cd]indole Into a 500-ml autoclave were added 1-benzoyl-4-(trifluoroacetyl)amino-6-bromo-1,2,2a,3,4, 5-hexahydrobenz[cd]indole (453 mg, 1 mmole) bis,(triphenylphosphine)palladium chloride (50 mg) triethylamine (0.5 ml) and ethanol (200 ml). The autoclave was purged three times to 60 psig (4.22 Kg per square cm) with carbon monoxide and then pressurized to 100 psig (7.03 Kg per square cm) at room temperature. The mixture was heated to 120° C. and maintained at temperature for about 2 hours during which time the pressure increased to about 140 psig (9.84 Kg per square cm). The vessel was cooled, vented and opened to provide a clear solution. High pressure liquid chromatography of the reaction mixture showed only starting material and no reaction products. The reaction mixture was returned to the autoclave. An additional 0.5 ml of triethylamine was added along with 50 mg of bis(triphenylphosphine)palladium chloride. The autoclave was vented three times with carbon monoxide, pressured to 100 psig (7.03 Kg per square cm) and heated to 145° C. The pressure increased to 160 psig (11.25 Kg per square cm). The reaction mixture was maintained at about 130° C. overnight after cooling. Analysis of the reaction mixture by high pressure liquid chromatography showed essentially all of the starting material remained with only minor peaks corresponding to other materials present.

EXAMPLE 9

Preparation of
1-benzoyl-4-(trifluoroacetyl)amino-6-(dibenzylaminocarbonyl-1,2,2a,3,4,5-hexahydrobenz[cd]indole Into an autoclave were placed 1-benzyol-4-(trifluoroacetyl)amino-6-iodo-1,2,2a,3,4,5-hexahydrobenz[cd]indole (500 mg, 1.0 mmol), bis(triphenylphosphine)palladium bromide (16 mg, 0.02 mmol), dibenzylamine (460 ml, 2.4 mmol) and toluene (100 ml). The autoclave was sealed, purged three times with carbon monoxide and pressurized to 100 psig (7.03 Kg per square cm) with carbon monoxide. The vessel was heated to 100° C. and maintained at 100° C. and 100 psig (7.03 Kg per square cm) carbon monoxide atmosphere for 6 hours. Heating was terminated and the vessel was allowed to cool to room temperature and stand overnight. The vessel was vented, opened and the contents removed with the assembly rinsed with 30 ml of methylene chloride. 20 ml of 1.0 N HCl were added to the mixture and the mixture shaken to provide two layers containing tan solid. The organic phase was separated and extracted with two 25-ml aliquots of water. The organic phase was then dried over anhydrous sodium sulfate, filtered and the liquid evaporated under vacuum to provide about 630 mg of an orange solid. The solid was dissolved in an ethanol water mixture with heating. Upon cooling the solid crystals formed which were separated and rinsed with an ethanol-water mixture. The desired product was confirmed by comparison of HPLC retention time and NMR with known product.

EXAMPLE 10

Attempted preparation of
1-benzoyl-4-(di-n-propyl)amino-6-aminocarbonylhexahydrobenz[cd]indole Into a 500-ml autoclave were placed 1-benzoyl-4-(di-n-propyl)amino-6-bromo-hexahydrobenz[cd]indole (500 mg, 1.13 m moles), bis(triphenylphosphine)palladium chloride (40 mg, 0.057 mmoles), and toluene (100 ml). The autoclave was sealed, purged three times with carbon monoxide at room temperature. The autoclave was cooled to about 15° C. with stirring of the contents. Anhydrous ammonia was introduced into the autoclave with stirring at 15° C. to a pressure of about 60 psig (4.22 Kg per square cm). Carbon monoxide gas was then introduced into the autoclave with stirring at about 15° C. to a final pressure of about 130 psig (9.14 Kg per square cm). The autoclave was heated to about 100° C. with stirring to provide in initial pressure at 100° C. of about 300 psig (21.1 Kg per square cm). Reaction temperature was maintained at about 100° C. for five hours with a final pressure after 5 hours of about 240 psig (16.9 Kg per square cm). The autoclave was cooled to about 24° C., vented and the contents analyzed by high pressure liquid chromatography which showed that essentially no reaction had taken place. The autoclave containing the original starting materials was resealed and purged three times with carbon monoxide gas. The autoclave was cooled to about 15° C. with stirring and an hydrous ammonia was introduced into the autoclave with stirring at about 15° C. to a pressure of about 50 psig (3.52 Kg per square cm). Carbon monoxide gas was then introduced into the autoclave with stirring at about 15° C. to a final pressure of about 150 psig (10.5 Kg per square cm). The autoclave was sealed and heated to about 160° C. and maintained at that temperature with stirring for about five hours. The initial pressure at 160° C. was about 400 psig (28.1 Kg per square cm). After five hours the heating was stopped and the vessel allowed to cool to room temperature over night. The reaction mixture was analyzed by high pressure liquid chromatography which showed that about 10% of the starting material had been converted to the desired 6-aminocarbonyl product.

We claim:
1. A compound of the formula:

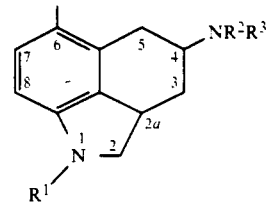

wherein
$R^1$ is hydrogen or an amino-protecting group;
$R^2$ is hydrogen, $C_1$-$C_4$ alkyl, allyl or an amino-protecting group; and
$R^3$ is hydrogen, $C_1$-$C_4$ alkyl, or allyl.

2. A compound of claim 1 wherein $R^1$ is an amino-protecting group; $R^2$ is hydrogen, an amino-protecting group, or n-propyl; and $R^3$ is hydrogen, methyl, ethyl or n-propyl.

3. A compound of claim 2 wherein $R^1$ is benzoyl, p-toluenesulfonyl, acetyl, trichloroacetyl, or trifluoroacetyl; $R^2$ is hydrogen, trifluoroacetyl, or n-propyl; and $R^3$ is hydrogen or n-propyl.

4. The compound of claim 3 wherein $R^1$ is benzoyl, $R^2$ is trifluoroacetyl, and $R^3$ is n-propyl.

5. The compound of claim 3 wherein $R^1$ is benzoyl, $R^2$ is trifluoroacetyl, and $R^3$ is hydrogen.

6. The compound of claim 3 wherein $R^1$ is benzoyl, $R^2$ is hydrogen, and $R^3$ is n-propyl.

7. The compound of claim 3 wherein $R^1$ is benzoyl, $R^2$ is n-propyl, and $R^3$ is no-propyl.

8. The compound of claim 7 consisting of the enantiomer wherein the 2a-position is in the R configuration and the 4-position is in the R configuration.

* * * * *

UNITED STATES PATENT AND TRADEMARK OFFICE
CERTIFICATE OF CORRECTION

PATENT NO. : 5,039,820

DATED : August 13, 1991

INVENTOR(S) : Thomas J. Kress and James P. Wepsiec

It is certified that error appears in the above-identified patent and that said Letters Patent is hereby corrected as shown below:

Column 6, line 42 "Formula I, 1-benzoyl" should read
-- Formula I, (2a-R,4-S)-1-benzoyl --.

Column 18, lines 21-29 figure

"
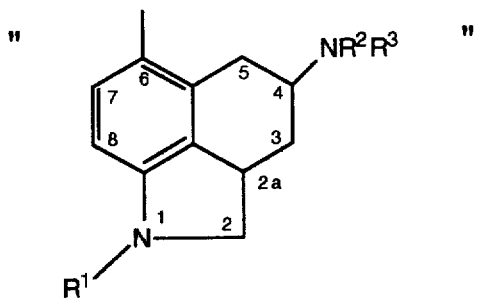
"

should read

--
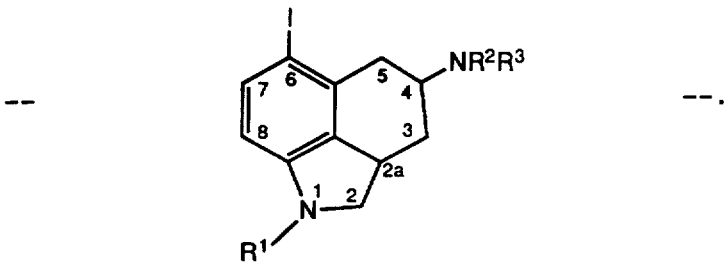
--.

UNITED STATES PATENT AND TRADEMARK OFFICE
CERTIFICATE OF CORRECTION

PATENT NO.  : 5,039,820

DATED       : August 13, 1991

INVENTOR(S) : Thomas J. Kress and James P. Wepsiec

It is certified that error appears in the above-identified patent and that said Letters Patent is hereby corrected as shown below:

Column 18, line 54 "is no-propyl" should read -- is n-propyl --.

Column 18, line 57 "the R configuration" should read -- the S configuration --.

Signed and Sealed this

Sixteenth Day of March, 1993

Attest:

STEPHEN G. KUNIN

*Attesting Officer*      Acting Commissioner of Patents and Trademarks